US00PP28922P2

(12) United States Plant Patent
Bullis

(10) Patent No.: US PP28,922 P2
(45) Date of Patent: Jan. 30, 2018

(54) ***AECHMEA* PLANT NAMED 'DEL CIELO'**

(50) Latin Name: ***Aechmea fendleri*×*Aechmea dichlamydea trinitensis***
Varietal Denomination: Del Cielo

(71) Applicant: Patricia Gomez Bullis, Princeton, FL (US)

(72) Inventor: Patricia Gomez Bullis, Princeton, FL (US)

(73) Assignee: Bullis Bromeliads, Princeton, FL (US)

( * ) Notice: Subject to any disclaimer, the term of this patent is extended or adjusted under 35 U.S.C. 154(b) by 0 days.

(21) Appl. No.: 15/330,207

(22) Filed: Aug. 22, 2016

(51) Int. Cl.
*A01H 5/02* (2006.01)

(52) U.S. Cl.
USPC ..... Plt./370

(58) Field of Classification Search
USPC ..... Plt./370
See application file for complete search history.

*Primary Examiner* — Anne M Grunberg
(74) *Attorney, Agent, or Firm* — C. A. Whealy

(57) ABSTRACT

A new and distinct cultivar of *Aechmea* plant named 'Del Cielo', characterized by its upright and outwardly arching growth habit; creamy white, light green and green variegated leaves with green-colored margins and creamy white and yellow green-colored longitudinal stripes; inflorescences held upright and above the foliar plane on strong red-colored scapes; tightly branched inflorescences with dark violet blue-colored petals and lighter violet blue-colored sepals; and long-lasting inflorescences.

1 Drawing Sheet

Botanical designation: *Aechmea fendleri*×*Aechmea dichlamydea trinitensis.*

Cultivar denomination: 'DEL CIELO'.

BACKGROUND OF THE INVENTION

The present invention relates to a new and distinct *Aechmea* plant, botanically known as *Aechmea fendleri*×*Aechmea dichlamydea trinitensis* and hereinafter referred to by the cultivar name 'Del Cielo'.

The new *Aechmea* plant is a naturally-occurring whole plant mutation of the *Aechmea fendleri*×*Aechmea dichlamydea trinitensis* 'Del Mar', disclosed in U.S. Plant Pat. No. 13,421. The new *Aechmea* plant was discovered and selected by the Inventor from within a population of plants of 'Del Cielo' in a controlled greenhouse environment in Princeton, Fla. in 2005.

Asexual reproduction of the new *Aechmea* plant by offsets in a controlled greenhouse environment in Princeton, Fla. since 2005 has shown that the unique features of this new *Aechmea* plant are stable and reproduced true to type in successive generations.

SUMMARY OF THE INVENTION

Plants of the new *Aechmea* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Del Cielo'. These characteristics in combination distinguish 'Del Cielo' as a new and distinct *Aechmea* plant:

1. Upright and outwardly arching growth habit.
2. Creamy white, light green and green variegated leaves with green-colored margins and creamy white and yellow green-colored longitudinal stripes.
3. Inflorescences held upright and above the foliar plane on strong red-colored scapes.
4. Tightly branched inflorescences with dark violet blue-colored petals and lighter violet blue-colored sepals.
5. Long-lasting inflorescences.

Plants of the new *Aechmea* differ from plants of the parent, 'Del Mar', primarily in leaf color as plants of 'Del Mar' have solid green-colored leaves.

Plants of the new *Aechmea* can be compared to plants of *Aechmea fendleri*×*Aechmea dichlamydea trinitensis* 'America', disclosed in U.S. Plant Pat. No. 27,762. Plants of the new *Aechmea* and 'America' differ primarily in the following characteristics:

1. Plants of the new *Aechmea* are more compact and have shorter leaves than plants of 'America'.
2. Inflorescences of plants of the new *Aechmea* are more dense than inflorescences of plants of 'America'.

BRIEF DESCRIPTION OF THE PHOTOGRAPHS

The accompanying colored photographs illustrate the overall appearance of the new *Aechmea* plant showing the colors as true as it is reasonably possible to obtain in colored reproductions of this type. Colors in the photographs may differ slightly from the color values cited in the detailed botanical description which accurately describe the colors of the new *Aechmea* plant.

The photograph on the right side of the sheet is a side perspective view of a typical flowering plant of 'Del Cielo' grown in a container.

The photograph on the left side of the sheet is a close-up view of a typical inflorescence of 'Del Cielo'.

DETAILED BOTANICAL DESCRIPTION

The aforementioned photographs and following observations, measurements and values describe plants grown in 20-cm containers during the summer in a polypropylene-covered shadehouse in Princeton, Fla. During the production of the plants, day temperatures ranged from 28° to 30° C., night temperatures ranged from 18° C. to 22° C. and light levels ranged from 2,200 to 3,200 foot-candles. Plants were 14 months old when the photographs and description were taken. In the following description, color references are made to The Royal Horticultural Society Colour Chart, 2007 Edition, except where general terms of ordinary dictionary significance are used.

Botanical classification: *Aechmea fendleri*×*Aechmea dichlamydea trinitensis* 'Del Cielo'.

Parentage: Naturally-occurring whole plant mutation of the *Aechmea fendleri*×*Aechmea dichlamydea trinitensis* 'Del Mar', disclosed in U.S. Plant Pat. No. 13,421.

Propagation:

*Type*.—By offsets.

*Time to initiate roots, summer*.—About 30 to 45 days at temperatures ranging from 28° C. to 30° C.

*Time to initiate roots, winter*.—About 45 to 60 days at temperatures ranging from 28° C. to 30° C.

*Time to produce a rooted young plant, summer*.—About three months at temperatures ranging from 28° C. to 30° C.

*Time to produce a rooted young plant, winter*.—About six months at temperatures ranging from 18° C. to 22° C.

*Root description*.—Medium in thickness, fibrous; yellow and white in color, actual color of the roots is dependent on substrate composition, water quality, fertilizer type and formulation, substrate temperature and physiological age of roots.

*Rooting habit*.—Moderately freely branching; medium density.

Plant description:

*Plant and growth habit*.—Upright and outwardly arching growth habit; rosette leaves are erect when young, becoming outwardly arching with development; plants readily produce offsets; vigorous growth habit.

*Plant height, soil surface to top of leaf canopy*.—About 53.3 cm.

*Plant height, soil surface to top of inflorescence*.—About 69.8 cm.

*Plant diameter or spread*.—About 81.3 cm.

Leaf description:

*Arrangement*.—Rosette, spiral phyllotaxis; leaves clasping and sessile; simple.

*Length*.—About 60 cm.

*Width*.—About 6.7 cm; at the base, about 11.5 cm.

*Shape*.—Lanceolate, strap-like with a broad sheathing base.

*Apex*.—Cuspidate.

*Base*.—Truncate.

*Margin*.—Serrate and spinose.

*Aspect*.—Upright to arching with development.

*Texture, upper and lower surfaces*.—Smooth, glabrous; leathery; stiff.

*Luster, upper and lower surfaces*.—Lustrous.

*Venation*.—Parallel.

*Color*.—Developing leaves, upper and lower surfaces: Close to 146C to 146D; towards the base, close to 145D. Fully expanded leaves, upper surface: Towards and at the margins, close to 146B; central parallel longitudinal stripes, close to 158C and close to 145A to 145B; venation, close to 146B to 146C. Fully expanded leaves, lower surface: Towards the margins, close to 146B; central parallel longitudinal stripes, close to 158D and close to 145B; venation, close to 146C to 146D.

Inflorescence description:

*Inflorescence form and arrangement*.—Long, open terminal panicles with tightly branched lateral panicles supported by erect and strong scapes; about 70 lateral panicles each with about twelve individual flowers; flowers distichous, sessile.

*Time to flower*.—Plants begin flowering about 12 to 16 weeks after planting.

*Inflorescence longevity*.—Inflorescences of the new *Aechmea* are very long-lasting, typically bract color will be maintained for about two months in the interior and about five months in the landscape depending on environmental conditions; inflorescences persistent.

*Fragrance*.—None detected.

*Inflorescence length*.—About 36 cm.

*Inflorescence width*.—About 12.5 cm.

*Flower buds*.—Length: About 1 cm. Diameter: About 6 mm. Shape: Ovoid, pointed. Texture and luster: Smooth, glabrous; semi-glossy. Color: Close to 97A; towards the base, close to 97B; bract, close to N92B.

*Flower length*.—About 1.6 cm.

*Flower diameter*.—About 4 mm.

*Petals*.—Quantity and arrangement: Three in a single whorl. Length: About 1.6 cm. Width: About 3 mm. Shape: Elongated ovate to lanceolate. Apex: Acute to mucronate. Base: Attenuate. Margin: Entire. Texture and luster, inner and outer surfaces: Smooth, glabrous; semi-glossy. Color: When opening, inner and outer surfaces: Distally, close to 90A; proximally, close to 91B. Fully opened, inner and outer surfaces: Distally, close to N92B; proximally, close to 91B; venation, close to 91B; color does not change with development.

*Sepals*.—Quantity and arrangement: Three in a single whorl; imbricate and tightly appressed to the petals. Length: About 1.4 cm. Width: About 5 mm. Shape: Pointed ovate to lanceolate. Apex: Apiculate. Base: Truncate. Margin: Entire. Texture, inner and outer surfaces: Smooth, glabrous. Luster, inner surface: Slightly glossy to semi-glossy. Luster, outer surface: Glossy. Color: When opening and fully opened, inner surface: Close to 93D. When opening and fully opened, outer surface: Close to 96B.

*Scapes*.—Length to base of inflorescence: About 32 cm. Diameter: About 1.2 cm. Strength: Strong. Aspect: Upright. Texture and luster: Farinose; matte. Color: Close to N34C and 46D.

*Reproductive organs*.—Stamens: Quantity per flower: Six. Filament length: About 4 mm. Filament color: Close to 155D. Anther size: About 1 mm by 2 mm. Anther shape: Lanceolate. Anther color: Close to 155B. Pollen: None observed. Pistils: Quantity per flower: One. Pistil length: About 2 mm. Style length: About 1 mm. Style color: Close to 196B. Stigma diameter: About 1 mm. Stigma shape: Rounded. Stigma color: Close to 91C. Ovary color: Close to 196D.

*Seeds*.—Seed production has not been observed on plants of the new *Aechmea*.

Temperature tolerance: Plants of the new *Aechmea* have been observed to tolerate temperatures ranging from about 3° C. to about 36° C.

Disease & pest resistance: Plants of the new *Aechmea* have been observed to be resistant to *Pythium*. Plants of the new *Aechmea* not been observed to be resistant to pests and other pathogens common to *Aechmea* plants.

It is claimed:

1. A new and distinct *Aechmea* plant named 'Del Cielo' as illustrated and described.

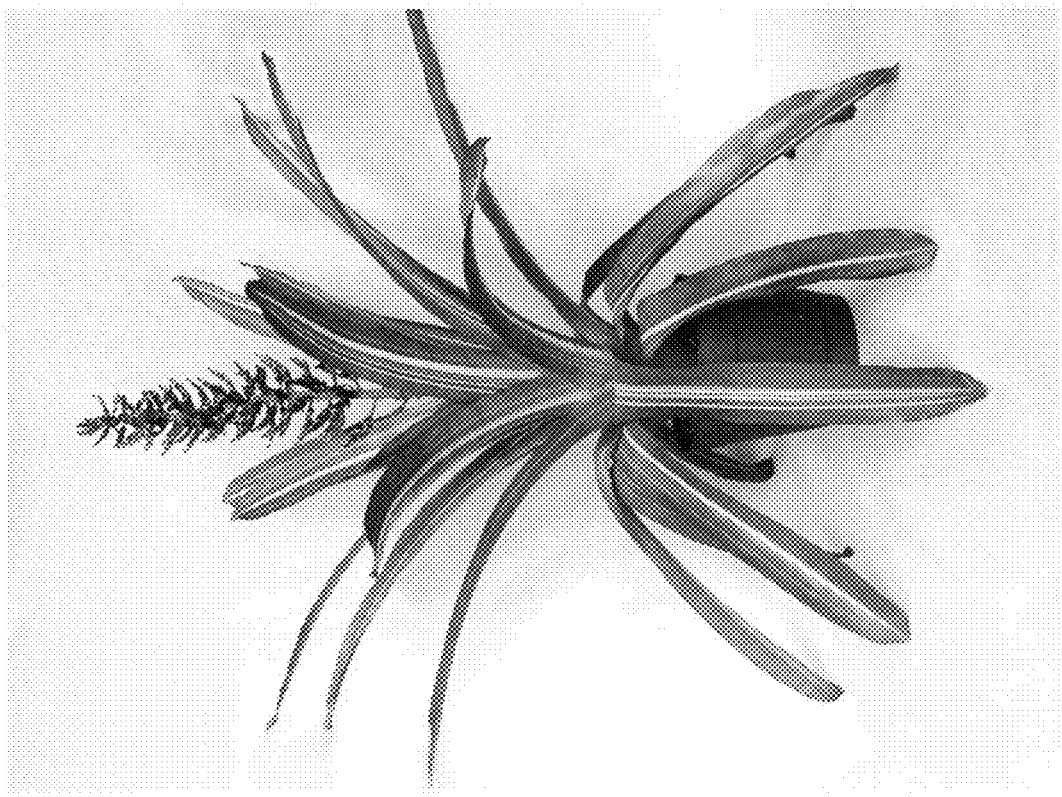
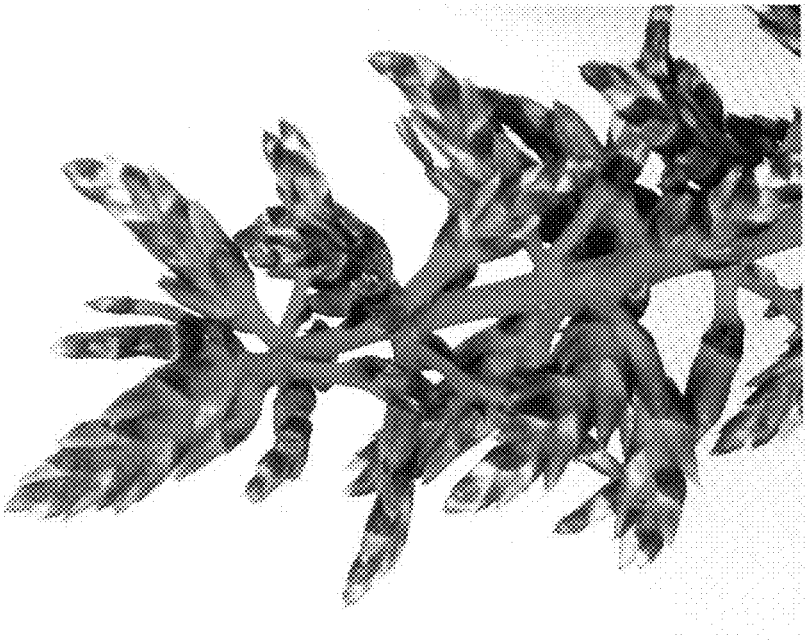

* * * * *